United States Patent [19]

Hsiao

[11] Patent Number: 4,508,702

[45] Date of Patent: Apr. 2, 1985

[54] SUSTAINED RELEASE ASPIRIN

[75] Inventor: Charles H. Hsiao, Miami, Fla.

[73] Assignee: Key Pharmaceuticals, Inc., Miami, Fla.

[21] Appl. No.: 576,777

[22] Filed: Feb. 3, 1984

Related U.S. Application Data

[63] Continuation of Ser. No. 388,183, Jun. 14, 1982, abandoned.

[51] Int. Cl.³ .................. A61K 9/20; A61K 9/28; A61K 9/48
[52] U.S. Cl. ........................ 424/19; 424/22; 424/37
[58] Field of Search .................. 424/19-22

[56] References Cited

U.S. PATENT DOCUMENTS

| | | | |
|---|---|---|---|
| 2,811,483 | 10/1957 | Aterno et al. | 167/81 |
| 2,853,420 | 9/1958 | Lowey | 167/82 |
| 2,887,440 | 5/1959 | Greminger et al. | 424/35 |
| 2,928,770 | 3/1960 | Bardani | 167/82 |
| 3,081,233 | 3/1963 | Enz et al. | 167/82 |
| 3,109,775 | 11/1963 | Shepard et al. | 167/82 |
| 3,133,863 | 5/1964 | Tansey | 424/35 |
| 3,247,066 | 4/1966 | Milosovich | 167/82 |
| 3,256,111 | 6/1966 | Singiser | 424/35 |
| 3,341,416 | 9/1967 | Anderson et al. | 424/35 |
| 3,344,029 | 9/1967 | Berger | 167/82 |
| 3,383,236 | 5/1968 | Brindamour | 424/35 |
| 3,388,041 | 6/1968 | Gans et al. | 424/35 |
| 3,400,185 | 9/1968 | Kohnle et al. | 264/117 |
| 3,488,418 | 1/1970 | Holliday et al. | 424/35 |
| 3,524,910 | 8/1970 | Holliday et al. | 424/35 |
| 3,632,739 | 1/1972 | Kornblum | 424/20 |
| 3,773,920 | 11/1973 | Nakamoto et al. | 424/19 |
| 3,835,221 | 9/1974 | Fulberth et al. | 424/20 |
| 3,907,983 | 9/1975 | Seth | 424/35 |
| 3,917,813 | 11/1975 | Pedersen | 424/35 |
| 3,922,339 | 11/1975 | Shear | 424/19 |
| 3,951,851 | 4/1976 | Kitajima | 424/35 |
| 4,016,254 | 4/1977 | Seager | 424/271 |
| 4,083,949 | 4/1978 | Benedickt | 424/19 |
| 4,138,475 | 2/1979 | McAinsh et al. | 424/20 |
| 4,167,558 | 9/1979 | Sheth et al. | 424/35 |
| 4,173,626 | 11/1979 | Dempski et al. | 424/19 |
| 4,248,858 | 2/1981 | Guley et al. | 424/21 |
| 4,259,314 | 3/1981 | Lowey | 424/19 |
| 4,321,253 | 3/1982 | Beatty | 424/35 |
| 4,341,759 | 7/1982 | Bogentoft et al. | 424/21 |

FOREIGN PATENT DOCUMENTS 109438  1/1940  Australia ............... 424/20

OTHER PUBLICATIONS

Green et al., Chem. Abstr. 95 #12703f, Jul. 13, 1981 of J. Pediatr. (1981) 98(5):832-834 Absorption Characteristics of Sustained Release Theophylline Capsules Administered in Apple Sauce.

Green et al., J. Pediatrics 98(5):832-834, May 1981 "Absorption Characteristics of Sustained Release Theophylline Capsules Administered in Apple Sauce".

Weinberger J. Pediatrics 92(1):1-7, Jan. 1978 Theophylline for Treatment of Asthma.

*Primary Examiner*—Shep K. Rose
*Attorney, Agent, or Firm*—Wegner & Bretschneider

[57] ABSTRACT

A sustained release aspirin dosage form permits the continuous delivery of aspirin into the gastrointestinal tract for a period of at least eight hours. The sustained release aspirin dosage form comprises a plurality of polymerically coated aspirin crystals each of which comprises an aspirin seed. The majority of aspirin seeds have a mesh size of from about 30 to about 60 mesh. Each of the aspirin seeds is individually coated with a polymeric mixture, which comprises from about 1.5 to about 15 parts by weight ethylcellulose and about one part by weight hydroxypropylcellulose.

5 Claims, No Drawings

SUSTAINED RELEASE ASPIRIN

This application is a continuation application of U.S. application Ser. No. 388,183, filed June 14, 1982, now abandoned.

In accordance with the present invention there is provided a sustained release aspirin preparation, which comprises a plurality of crystals which disperse in the gastrointestinal tract to avoid localized irritation, the coated crystals also providing a sustained release with the release of the aspirin over a period of at least about eight hours, thereby reducing the application of aspirin to a patient in need thereof. While readministration of aspirin for headaches may not pose a major inconvenience, it is to be particularly noted that for an adult suffering from arthritis who may need an at least eight hour protection to avoid being wakened from the pain of such arthritis (or other chronic disease) during a normal period of overnight sleep, the provision of a sustained release form that provides an at least eight hour protection is highly desirable. Instead of waking in the early morning hours due to pain caused when the effect of normal aspirin taken before retiring has worn off, with the sustained release aspirin preparation of the present invention it is possible for the pain relief to last until the normal waking time of the patient, permitting an unbroken sleeping pattern throughout the night. In addition to the use of the instant sustained release aspirin for those suffering from arthritis and other chronic illnesses, another important use of the coated crystals of the present invention is pediatric, to provide an "overnight" dosage of aspirin for small children who often run high fevers and, without such an overnight dosage, would be awakened in the middle of the night. In its generic aspect, the present invention provides a sustained release aspirin dosage form to permit the continuous delivery of aspirin into the gastrointestinal tract for a period of at least eight hours which comprises a plurality of polymerically coated aspirin crystals which each comprise an aspirin seed, the majority of aspirin seeds having a mesh size of from about 30 to about 60 mesh, each of said aspirin seeds being individually coated with a polymeric mixture which comprises from about 1.5 to about 15 parts by weight ethylcellulose and about one part by weight hydroxypropylcellulose. The dosage form may be, for example, a capsule, which in the case of an adult or older child may be taken whole and which dissolves in the stomach, there releasing the polymerically coated aspirin tablets. For smaller children or geriatric patients who either are unable or unwilling to swallow a whole capsule, the drug may be sprinkled onto food or mixed with a beverage and so taken, the polymeric coating masking the unpleasant taste of the aspirin. For this mode of administration the dosage form may be, for example, a capsule that is easily opened without difficulty, to avoid spilling of the contents. For example, a preferred embodiment of a capsule to be used merely to store the drug, and not necessarily to be swallowed, is disclosed in Keith, "Anti-Spilling Drug Capsule," United States patent application Ser. No. 338,257, filed Jan. 11, 1982, now U.S. Pat. No. 4,442,941, the entire specification of which is hereby incorporated by reference herein. In another embodiment of this aspect of the present invention, a sealed pouch preferably constructed of a polyester fiom (Mylar) may be used to house the polymerically coated aspirin crystals. Although the aspirin that is used as the "seed" for the present invention may be granulated or may be compounded with other conventional tableting ingredients, in accordance with a preferred aspect of the present invention it is contemplated that pure aspirin crystals may be used. The aspirin, furthermore, should have a relatively uniform particle size distribution, which has been found to be important to achieving relative linearity of release over a prolonged period of time. Accordingly, the aspirin "seeds" should be selected for a particle size which ranges from about 30 to about 60 mesh. It is contemplated that while minor amounts of the aspirin seeds may fall outside this range, the number of such particles should be minimized, the predominant proportion of the total aspirin seeds being in the about 30 to about 60 mesh size range, particles outside that range being tolerated only to the extent that they do not destroy the relative linearity of release over the required period of at least about eight hours delivery of the aspirin in the gastrointestinal tract.

The polymeric coating requires a major component of ethylcellulose and a minor component of hydroxypropylcellulose, it being required that the weight ratio of ethylcellulose to hydroxypropylcellulose be at least about 2.5. Accordingly, in one aspect of the present invention it is contemplated that said weight ratio be from about 2.5:1 to about 15:1, with a preferred range being from about 3.5:1 to about 12:1, and still more preferably about 8:2. The combined weight of the polymeric coating is from about 3 to about 10% of the total weight of the polymerically coated aspirin crystal, and in a preferred embodiment is about 5% of such total weight.

While the total dosage in a dosage unit may vary dependent upon the ultimate use, it is contemplated that a single dosage unit form for adult use for a period of at least about eight hours is about 800 mg (325 mg=5 grain, the usual adult aspirin tablet), an adult taking one or two dosage units. In a typical dosage unit form there are present on the order of 1000 polymerically coated aspirin seeds.

The following examples serve to illustrate the invention:

EXAMPLE I 700 gm aspirin crystals, all having a size of between 30 and 60 mesh, are placed in a six inch air suspension coating column (Wurster column of manufacture by Glatt, West German) and coated with a mixture of 368 ml polymer solution in chloroform which contained 29.4 gm ethylcellulose ["Ethocel N-10" (Dow)] and 7.4 gm hydroxypropylcellulose ["Klucel LF" (Hercules)] and 92 ml methanol. The coating solution is sprayed at 2.5 bar pressure with the liquid feed rate of 60 ml/minute. The inlet air temperature is about 60° C. After completion of the feed of the coating, the quickly dried polymerically coated aspirin crystals are recovered from the bottom of the air suspension coating.

EXAMPLE II

The polymerically coated aspirin crystals of Example I are tested according to U.S. Pharmacopieia XX dissolution procedure. Thus, the test comprises a one hour residence in simulated gastric fluid, followed by residence in simulated intestinal fluid. The following release of aspirin was observed through this testing procedure, confirming the relatively linear release of the aspirin into this simulated gastrointestinal tract for a period of over ten hours:

| Aspirin release after | Percentage released |
| --- | --- |
| 1 hour | 11.5% |
| 2 | 30.7 |
| 4 | 53.5 |
| 6 | 69.8 |
| 8 | 84.6 |
| 10 | 96.2 |

The relatively linear release shown over the ten hour period indicates the use of the polymerically coated aspirin seeds of the present invention for uses requiring a sustained release for a period of at least eight hours.

What is claimed is:

1. In a sustained release aspirin easily openable housing capsule or sealed pouch dosage form to permit the sprinkling onto food or mixing with a beverage, and, upon ingestion of said food or beverage, the continuous delivery of taste-masked aspirin into the gstrointestinal tract for a period of at least eight hours, the improvement consisting of a plurality of polymerically taste-masked coated aspirin crystal seeds each having therein a seed of pure aspirin as such, the majority of aspirin seeds having a mesh size of from about 30 to about 60 mesh, each of said otherwise unpleasant tasting aspirin seeds being individually coated with a polymeric mixture consisting of from about 1.5 to about 15 parts by weight ethyl cellulose and about one part by weight hydroxypropyl cellulose, and wherein the weight of the coating constitutes from about 3 to about 10% by weight of the said coated aspirin seeds.

2. A sustained release aspirin dosage form of claim 1, wherein said dosage form is in the form of a housing capsule.

3. A sustained release dosage form of claim 1, wherein said dosage form is in the form of a sealed pouch.

4. A sustained release aspirin dosage form of claim 1, wherein the weight ratio between the ethyl cellulose and hydroxypropyl cellulose is from about 3.5:1 to about 12:1.

5. A sustained release aspirin dosage form of claim 4, wherein said weight ratio is about 8:2.

* * * * *